United States Patent [19]

Kubota et al.

[11] Patent Number: 5,229,147
[45] Date of Patent: Jul. 20, 1993

[54] COATED VITAMIN C PREPARATION FOR ANIMAL FEED, PRODUCTION AND USE THEREOF

[75] Inventors: Saburoh Kubota; Takaaki Hisamoto; Koichi Iwanami, all of Tokyo, Japan

[73] Assignees: Nippon Oil and Fats Co., Ltd.; Eisai Co., Ltd., both of tokyo, Japan

[21] Appl. No.: 650,731

[22] Filed: Feb. 5, 1991

[30] Foreign Application Priority Data

Feb. 20, 1990 [JP] Japan .................................. 2-39359
Jan. 21, 1991 [JP] Japan .................................. 3-5311

[51] Int. Cl.$^5$ .............................................. A23K 1/00
[52] U.S. Cl. .......................................... 426/2; 426/72; 426/99; 426/307; 426/310; 426/311; 426/805; 426/807
[58] Field of Search ................ 426/2, 72, 310, 311, 426/98, 99, 541, 307, 805, 807

[56] References Cited

U.S. PATENT DOCUMENTS 3,957,966 5/1976 Valan ................................. 426/311
4,187,322 2/1980 Josse et al. ........................ 426/72

FOREIGN PATENT DOCUMENTS 125894 11/1984 European Pat. Off. .
176772 4/1986 European Pat. Off. .
231817 8/1987 European Pat. Off. .

OTHER PUBLICATIONS

Ueno et al. "Feed for fish farming" Japio Abstract Accession No. 83-205461.
Iwanami et al. "Production of Coated Amino Acids" Japio Abstract Accession No. 89-002554.
Hawley "The Condensed Chemical Dictionary" 10th Edition Van Nostrand Reinhold Company (1982) p. 1029.
CA, vol. 110:133956C, Apr. 18, 1989, Coated organic acids or organic acid salts as food or feed additive. Iwanami, p. 599.
CA, vol. 102:77536m, Nov. 21, 1984, Protection of vitamins, Perry, p. 448.
Derwent Abstracts WPIL AN 88-231490, Coated inorganic acid or salt prepn. by contacting lipid powder with the acid or salt.
Patent Abstract of JP-A-63-164863.
ESA Chemabs No. 10133956, Coated organic acid or organic acid salts as food or feed additive, Iwanami.
Patent Abstracts of Japan, vol. 12, No. 438 (C-544) [3285], Nov. 17, 1988, "Production of Coated Organic Acid and Organic Acid Salt Preparation".

Primary Examiner—R. B. Penland
Attorney, Agent, or Firm—Flynn, Thiel, Boutell & Tanis

[57] ABSTRACT

A coated vitamin C preparation for animal feed comprises a particulate core containing vitamin C and a coating material composed of one or more fine powdery lipids having a melting point of at least 40° C. and containing vitamin E. The coating material is present as an agglomerated coating layer surrounding the entire circumference of each particle of the particulate core.

The coated vitamin C preparation is produced by a process, which comprises a step of bringing particles of a particulate core containing vitamin C into colliding contact with particles of a coating material composed of one or more fine powdery lipids having a melting point of at least 40° C. and containing vitamin E, so as to form a coating layer of agglomerated particles of the coating material surrounding the entire circumference of each particle of the core.

The coated vitamin C preparation is useful as a supplement to feeds for animals, such as, livestock, poultry and marine animals, by admixing same with the feed.

The coated vitamin C preparation is superior, as compared with conventional coated preparations, in the coverage performance, vitamin C isolation effect against external influences of, such as, light, heat, moisture and atmosphere, and gives better preservation of the vitamin C activity, even upon admixing with feed mixtures, and enables the high absorbability of vitamin C by organisms.

6 Claims, No Drawings

5,229,147

COATED VITAMIN C PREPARATION FOR ANIMAL FEED, PRODUCTION AND USE THEREOF

FIELD OF THE INVENTION

The present invention relates to a coated vitamin C preparation for animal feed and the process for the production and use thereof. More particularly, the present invention relates to a coated vitamin C preparation for animal feed, which is in the form of particles having a core containing vitamin C coated by a lipid layer, as well as to a process for the production and use thereof.

BACKGROUND OF THE INVENTION

Vitamin C has widely been incorporated into animal feeds both as a vitamin C supplement and as an antioxidant. The physiological activity of vitamin C decreases with the influence of atmosphere and moisture and by the action of light, heat and co-existing substances, such as metal ions etc. Thus, the vitaminic effectivity thereof is apt to be destroyed easily.

Under these circumstances, attempts had been made to provide a coated granular vitamin C preparation capable of preventing the activity decrease of vitamin C.

The hitherto proposed methods for preparing coated or encapsulated products of water-soluble vitamins inclusive of vitamin C can be classified into the following two generalized ways:

The first way comprises the steps of preparing an oil suspension of a particulate product of a water-soluble vitamin in a melt of a coating material composed of, for example, hardened oil, wax etc., spraying the resulting oil suspension using a spraying device or a rotary disc and solidifying the droplets formed by spraying by cooling, so as to form solid encapsulated particles of the water-soluble vitamin within a coverage layer of the coating material (See, for example, "Raw Feed Composition for Fish Cultivation" described in the Japanese Patent Publication No. 13192/1975, "Feeds for Fish Cultivation" given in the Japanese Patent Application Kokai No. 205461/1983 and so on).

The second way consists of a so-called fluidized bed process which comprises the steps of forming a gaseous suspension of a particulate product of a water-soluble vitamin in a pneumatically fluidized layer by an airstream blown up from the bottom of a fluidizing apparatus and spraying a solution of a coating material, such as a hardened fatty oil, wax etc., in a volatile solvent into the fluidized layer as a mist or liquid droplets from the side or upper portion of the fluidized layer to effect coating of the vitamin particles and evaporate off the solvent to dry the coating layer, or similar procedures using a fluidizing apparatus (See, for example, "Process for Effecting Coating of Particulate Product of Vitamin" as given in the Japanese Patent Application Kokai No. 52221/1975).

As to the coating material to be employed for producing coated or encapsulated particulate preparation of vitamins, there have been disclosed numerous studies, such as for example, "Method for Stabilizing L-Ascorbic Acid and its Salts" with the use of hardened fatty oils, lecithin and glycerin fatty acid monoesters, as given in Japanese Patent Publication No. 16779/1981; "Feeds for Fish Cultivation" with the use of higher fatty acids, as disclosed in Japanese Patent Application Kokai No. 205461/1983; "Thiamin Preparation for Fish Cultivation" with the use of waxes, as disclosed in Japanese Patent Application Kokai No. 157020/1984 and so on.

The conventional coated vitamin C preparations for animal feeds have disadvantages, such as for example, insufficient coverage performance, low content of vitamin C in the preparation with the concomitant necessity of a large application rate, poor conservation of vitamin C activity, lower absorbability of vitamin C by organisms and so on.

On the other hand, there has been proposed a method for coating over the entire circumferential surface of each particle of a pulverous product of amino acids as a core material with a layer of a powdery product of a lipid having a melting point of at least 40° C. as a coating material by causing the particles of the coating material to adhere uniformly onto the surface of particle of the core material (Japanese Patent Application Kokai No. 2554/1989). If this method is applied to effect coating of particles of a pulverous vitamin C product, no coated vitamin C preparation exhibiting a superior preservation of vitamic activity can be obtained.

SUMMARY OF THE INVENTION

An object of the present invention is to eliminate the above disadvantages of the stand and techniques and to provide a coated vitamin C preparation for application to animal feeds which exhibits a high absorbability of vitamin C by organisms and superior coverage performance by providing very effective isolation of the vitamin C core from external influences, such as, atmosphere, moisture, light, heat and so on, thereby providing superior preservation of the physiological activity of vitamin C while also being capable of attaining a high content of vitamin C thereby allowing the reduction of the application rate in the feed.

The coated vitamin C preparation for animal feed according to the present invention comprises a particulate core substance essentially of, or containing, vitamin C and a coating material composed of a fine powdery product of one or more lipids having a melting point of at least 40° C. and a content of vitamin E for coating the vitamin C core particles over the entire circumference of the particle.

The coated vitamin C preparation according to the present invention is produced by bringing the particles of the vitamin C core substance into colliding contact with the fine particles of the coating material having a melting point of at least 40° C. and a content of vitamin E, so as to form a coating layer by the coating material to enclose the vitamin C particle therein.

The coated vitamin C preparation according to the present invention is utilized for supplementing feeds for livestock, poultry, marine culture animals by admixing it with the feeds.

DETAILED DESCRIPTION OF THE INVENTION

The particulate vitamin C product to be employed as the core substance of the coated vitamin C preparation according to the present invention may be either a product from natural material or a synthesized product existing in the form of powder or particles at ordinary temperature. The particulate vitamin C product may either be crystalline or amorphous. This particulate vitamin C product can be utilized as such as the raw material of the core substance of the coated preparation according to the present invention, while it is, of course possible to incorporate a preliminary granulation or pre-coating of the particulate or powdery vitamin C product with other components, such as, water-soluble materials, fatty substances and so on, for use as the core substance.

Concrete examples of the particulate vitamin C product include those of L-ascorbic acid, DL-ascorbic acid, araboascorbic acid, L-glucoascorbic acid, L-rhamnoascorbic acid and 6-desoxyascorbic acid; salts of these acids with metal cations, such as, calcium, sodium, potassium and so on; esters of these acids with, such as, phosphoric acid, acetic acid, sulfuric acid, fatty acids and derivatives, such as, metal salts etc., of these esters. These products can be employed solely or in combination of two or more of them for the core substance of the coated preparation according to the present invention.

For the water-soluble components which can be employed for the above-mentioned preliminary granulation or pre-coating of the particulate vitamin C product, there may be enumerated, for example, sugars, proteins, amino acids, inorganic salts and so on. As the fatty substances, there may be employed various lipids, such as, natural fats and oils, hardened oils, waxes, fatty acid monoglycerides, fatty acid diglycerides and fatty acids. Other components which can be employed are organic and inorganic high molecular weight substances of natural or synthetic nature.

The content of vitamin C in the starting particulate core substance should be at least 10% by weight, preferably at least 50% by weight. The particle size of the particulate starting core substance may be in the range of from 0.1 to 1,000 $\mu$m, preferably in the range of from 10 to 700 $\mu$m.

The coating material to be employed in the coated preparation according to the present invention may be a particulate lipid material having a melting point of at least 40° C. and a content of vitamin E.

As the lipid to be incorporated in the coated vitamin C preparation according to the present invention, there may be enumerated animal and vegetable oils, such as, soybean oil, palm oil, rapeseed oil, coconut oil, beef tallow, lard and so on; oils produced by micro-organisms; fatty acid esters, such as, fatty acid monoglycerides, fatty acid diglycerides, fatty acid propylene glycol esters and fatty acid sucrose esters; fatty acids and metal salts thereof; higher alcohols; waxes; phospholipids containing phosphrus and nitrogen; sugar lipids having sugar as a component; sulfolipids having a sulfo group; sterols; hydrocarbons; antioxidants, such as, ethoxyquin (6-ethoxy-1,2-dihydro-2,2,4-trimethylquinoline), butyl hydroxyanisole, butyl hydroxytoluene, tert-butyl hydroquinone, oryzanol and spice extract; fat soluble vitamins, such as, vitamin A, vitamin K and so on; and hardened materials of these lipids. These lipids can be employed alone or in mixture of two or more of them.

As the vitamin E component, products of either natural materials or synthesized material can be employed, above all, $\alpha$-, $\beta$-, $\gamma$- and $\delta$-tocopherols, esters of these with acetic acid, nicotinic acid and succinic acid. They are used individually or in a combination of one or more of them.

The coating material to be employed in the coated vitamin C preparation according to the present invention is composed of a fine powdery product of the above-mentioned lipid material having a melting point of at least 40° C. with an addition of a vitamin E component. The content of vitamin E in the coating material may be in the range of from 0.1 to 10%, preferably from 0.5 to 5%, based on the weight of the fine powdery coating material. The particle size of the fine powdery coating material may be in the range of from 0.1 to 100 $\mu$m, preferably from 0.5 to 50 $\mu$m.

The restriction as to the melting point of the fine powdery coating material is due to the practical requirement for attaining a coating over the core particle of vitamin C by a solid coverage layer of agglomerated particles of the fine powdery coating material at ordinary temperature. If the melting point is lower than 40° C., the solid discrete particulate state of the coated vitamin C preparation on storage at ordinary temperature will no longer be maintained.

The coated vitamin C preparation for animal feed according to the present invention is thus composed of a particulate core substance essentially of, or containing, vitamin C coated around its entire circumference with a layer of the lipid fine powdery coating material, whereby the particulate core substance is isolated effectively from external influences, such as ambient atmosphere etc. The coating layer is composed of an agglomerate of fine particles of the powdery lipid, which is distinguished from that of conventional preparations in which the coating layer is formed from a melt or solution of the coating material resulting in a successive filmy coverage layer.

A suitable weight proportion of the particulate core substance to the powdery coating material may be in the range from 0.1:1 to 50:1, preferably from 1:1 to 5:1.

A suitable ratio of particle size of the particulate core substance to that of the powdery lipid coating material may be in the range of from 0.1 to 10,000, preferably from 10 to 500.

The coated vitamin C preparation for animal feed according to the present invention is produced by causing the particles of the lipid fine powdery coating material having a melting point of at least 40° C. and a content of vitamin E to come into contact with particles of the core substance by collision, to thereby form a coating layer of an agglomerate of the particles of fine powdery coating material surrounding the entire circumference of each of the core particles.

Upon collision of the particles of the core substance with the fine particles of the coating material and the fine particles of the coating material with each other, the impinged portion of the fine particles of coating material will superficially melted and the particles will fuse together, whereby a tight coating layer is built up. As compared with the film-like continuous coating layer of conventional coated preparations in which the thickness of the coating layer is extremely thin at sharp portions, such as, edges, pointing ends etc., of the core particle where the coating layer will tend to be broken to expose the core, the coating layer of the coated vitamin C preparation according to the present invention formed by the collision of the particles provides a complete coverage of such sharp edges of the core particle, since the coating is effected by integration of fine particles under agglomeration, which tends to form a rounded contour.

For realizing contact of the fine particles of coating material with the particle of core substance by collision, various apparatuses can be utilized, such as, ball mills, electric mortars, high efficiency powder mixers, pnuematic high vortex apparatuses and so on (hereinafter denoted as coating devices). Care must be paid here for not causing excessively vigorous condition to occur in order to prevent the crushing or collapse of the core particle by the collisions. Thus, the collision of the particles may preferably be effected under such a mild condition that the core particles will not be broken and will be coated with agglomerates of fine particles of the powdery coating material over the entire circumference of the core particle by the partial melting of the collided fine particles and fusion with each other to form a tight integrated coating layer. Such a mild condition may be attained on a rotating mechanical coating device at a circumferential velocity not higher than 70 m/sec. Here, the temperature of the entire system of the coating device should not exceed above 40° C.

While it is possible to effect the colliding contact of the fine particles of coating material with the particles of the core substance by supplying both the starting materials directly to a coating device, an increase in the coverage performance may be attained when both the starting materials are first subjected to a premixing on a suitable device and the resulting pre-mixture supplied to the coating device to effect the intrinsic contact by collision. A further increase in the coverage performance will be realized when the coating material is supplied to the coating device in several aliquots to realize the colliding contact in multiple steps.

The mixing ratio of the core substance to the coating material (core substance/coating material weight ratio) may usually be in a range of from 0.1/1 to 50/1, which may preferably be adjusted in conjunction with the particle size ratio. If the particle size ratio of the core substance to the coating material is greater, the said mixing ratio can be settled at a high value, while the mixing ratio may preferably be settled at a low value if the paticle size ratio is smaller. However, the coverage performance will not simply increase by selecting the mixing ratio at a lower level, but a better performance may in some cases be attained even with a greater mixing ratio. With the same mixing ratio, an increase in the coverage performance will be attained by effecting the coating process in several steps by supplying the coating material under division into two or more aliquots.

The coated vitamin C preparation according to the present invention is useful for supplementing animal feeds by admixing it with conventional feed components as such so as to be received by, such as, livestock, poultry and marine culture animals. The rate of application or admixing of the coated vitamin C preparation according to the present invention depends on each specific animal, condition of the animal and so on, while an application rate of 0.0001-5%, calculated as pure substance of vitamin C, based on the total weight of the feed, as a general measure, may be practical.

The coated vitamin C preparation according to the present invention is superior in coverage performance, as compared with conventional coated preparations, for effectively isolating the vitamin C core particle from external influences of other components, radiant rays, heat, moisture and ambient atmosphere, and provides effectively preservation of the physiological activity of vitamin C for longer periods of time. The effectiveness of each component in the preparation is not destroyed by blunt mixing them with other feed materials for application. The absorbability of vitamin C of the preparation according to the present invention by animals is quite high. Thus, an efficient absorption of vitamin C by organisms can be attained.

According to the present invention, it is possible to increase the content of vitamin C in the coated preparation, thereby permitting a decrease in the rate of application, resulting in a lowering of the over-all feed cost.

By the process for producing the coated vitamin C preparation according to the present invention, coated vitamin C preparations exhibiting excellent properties as described above can easily and efficiently be obtained.

PREFERRED EMBODIMENTS OF THE INVENTION

The present invention will now be described by way of Examples, in which the values for per cent are based on a weight basis.

EXAMPLE 1

470 g of hardened rapeseed oil and 30 g of a mixed tocopherol concentrate [d-Mixed Tocopherols Concentrate 40 (trademark) of Eisai Co., Ltd.] were melted together and mixed homogeneously and the mixture was cooled and solidified. The resulting solid mixture was crushed into fine powder to prepare a fine powdery coating material having a melting point of 67.2° C. and an average particle size of 10 μm.

150 g of the above powdery coating material was supplied together with 350 g of a particulate product of L-ascorbic acid having an average particle size of 120 μm to a high efficiency powder mixer [NARA Hybridization System (trademark) of NARA Machinery Co., Ltd.] and worked up therein at a circumferential velocity of 13 m/sec at a water-cooling jacket temperature of 25° C. for 20 minutes. The resulting coated vitamin C preparation for animal feed was admixed with a kneaded feed for eel cultivation at an application rate of 1%, calculated as pure L-ascorbic acid, based on the weight of the kneaded feed, and the mixture was used in the cultivation of eel, while observing the L-ascorbic acid level in the blood of eel during cultivation, in order to assess the absorbability of L-ascorbic acid by the eel. The mixed kneaded feed prepared as above was administered to 10 eels by injecting the feed using a catheter into the stomach of each eel in an amount of 10 grams per 1 kilogram of the eel body weight and the ascorbic acid level in the blood was observed during the course of cultivation. The results are summarized in Table 1.

COMPARISON EXAMPLE 1

500 g of hardened rapeseed oil was solidified and crushed into fine powder to prepare a fine powdery coating material having a melting point of 67.3° C. and an average particle size of 10 μm.

Using this coating material, a coated vitamin C preparation was produced in the same manner as in Example 1 and similar absorbability tests were carried out on eel with it. Results are also given in Table 1.

TABLE 1

| | Absorbability of Vitamin C by Eel (mg/100 ml blood) | |
|---|---|---|
| Time after Administ. | Example 1 | Comparison Example 1 |
| 3 hr | 0.32 | 0.12 |
| 6 hr | 0.42 | 0.32 |
| 12 hr | 1.03 | 0.40 |

From Table 1, it is clear that the absorbability of vitamin C by eel is better as compared with the coated preparation of Comparison Example 1.

EXAMPLE 2

920 g of hardened soybean oil, 50 g of palm oil and 30 g of dl-α-tocopherol were melted together to form a homogeneous mixture. This mixture was cooled and solidified and the solid mixture was crushed into powder to prepare a fine powdery coating material having a melting point of 64.8° C. and an average particle size of 10 μm.

300 g of the above fine powdery coating material were supplied to a Henschel Mixer together with 700 g of a particulate product of L-ascorbic acid having an average particle size of 120 μm to work up at a circumferential velocity of 30 m/sec at a cooling jacket temperature of 20° C. for 15 minutes.

The thus obtained coated vitamin C preparation for animal feed was admixed with a kneaded feed for cultivating eel in an addition rate of 5%, calculated as pure L-ascorbic acid, based on the weight of the kneaded feed. Using this mixed feed, eels were cultivated and the L-ascorbic acid level in the blood of eel was observed in the same manner as in Example 1. The results are given in Table 2.

COMPARISON EXAMPLE 2

300 g of L-ascorbic acid were suspended in a fluidized layer on a pneumatic fluidized bed granulator at a fluidizing airstream temperature of 20°-25° C. and flow rate of 0.2 m³/min and, into the fluidizing layer thus formed, 200 g of a melt of hardened beef tallow were sprayed at a rate of 20 ml/min to obtain a coated L-ascorbic acid preparation.

Using this coated preparation, L-ascorbic acid absorbability tests were carried out on eel in the same manner as in Example 2. The results are recited in Table 2.

TABLE 2

| Time after Administ. | Absorbability of Vitamin C by Eel (mg/100 ml blood) | |
|---|---|---|
| | Example 2 | Comparison Example 2 |
| 6 hr | 1.23 | 0.92 |
| 12 hr | 1.84 | 1.54 |
| 24 hr | 0.81 | 0.64 |

From the results of Table 2, it is confirmed that the absorbability of vitamin C is superior for the coated vitamin C preparation of the present invention as compared with that of Comparison Example 2 on eel. While the difference in the absorbability seems not to be highly distinguishable, the effect over the retention duration is large for the coated preparation of the present invention.

EXAMPLE 3

0.5 g of the coated vitamin C preparation obtained in Example 2 was mixed with 225 g of wheat flour, 269.5 g of fish meal, 2.5 g of mineral components and 2.5 g of choline chloride and the mixture was treated using a Brabender Extruder at a barrel temperature of 80° C. with a water addition rate of 5%, in order to produce pelletized feed. The residual proportion of L-ascorbic acid (weight % remained) in the thus obtained pellet is given in Table 3.

COMPARISON EXAMPLE 3

The coated preparation obtained in Comparison Example 2 was worked up into pellets under the same condition as in Example 3, whereupon the residual proportion of L-ascorbic acid in the pellet obtained was determined. The result are given in Table 3.

TABLE 3

| | Vitamin C Preservation Effect | |
|---|---|---|
| | Example 3 | Comparison Example 3 |
| % remained | 74.0 | 65.9 |

From the results of Table 3, it is recognized that the vitamin C preservation effect is higher for the preparation of the present invention than that of Comparison Example 3.

EXAMPLE 4

The coated vitamin C preparation obtained in Example 2 was admixed at an additon rate of 0.1%, calculated as pure L-ascorbic acid, to a raw feed of mixer-minced raw sardine, whereupon the "strengthened" feed was stored at room temperature. The vitamin C content in the stored feed remaining in the course of storage was observed at intervals. The results are given in Table 4.

COMPARISON EXAMPLE 4

Calcium L-ascorbate was admixed at an addition rate of 0.1%, calculated as pure L-ascorbic acid, to the same feed employed in Example 4 and preservation of L-ascorbate was observed in the same manner as in Example 4. The results are given in Table 4.

COMPARISON EXAMPLE 5

The coated vitamin C preparation obtained in Comparison Example 2 was admixed at an addition rate of 0.1%, calculated as pure L-ascorbic acid, to the same feed employed in Example 4 and preservation of L-ascorbic acid was observed in the same manner as in Example 4. The results are given in Table 4.

COMPARISON EXAMPLE 6

In a melt of mixed oil (melting point 55° C.) composed of 360 g of hardened rapeseed oil and 840 g of hardened palm oil, 800 g of powdery L-ascorbic acid milled on a crusher to a particle size of below 20 μm was suspended. This oil suspension was sprayed into a cold airstream to form a coated pulverous preparation having a vitamin C content of 40%. Using this preparation, the same preservation tests as in Example 4 were carried out on the same feed. The results are given in Table 4.

TABLE 4

| Storage Period (hr) | Vitamin C Preservation Effect (Weight % of Remaining Vitamin C) | | | |
|---|---|---|---|---|
| | Example 4 | Comp. Example 4 | Comp. Example 5 | Comp. Example 6 |
| 1 | 100.0 | 91.2 | 84.9 | 97.5 |
| 3 | 100.0 | 62.1 | 64.9 | 96.0 |
| 5 | 100.0 | 52.4 | 60.1 | 80.3 |
| 12 | 99.4 | 48.0 | 48.8 | 48.5 |
| 24 | 98.7 | 28.2 | 20.8 | 40.1 |

EXAMPLE 5

The coated vitamin C preparation obtained in Example 2 was admixed, at an additon rate of 0.1%, calculated as pure L-ascorbic acid to a starting mass obtain moist pellets composed of 5:5 mixture of a raw feed of mixer minced raw sardine and a composite feed composed of 54% of fish meal, 45% of wheat flour, 0.5% of mineral components and 0.5% of choline chloride, whereupon the "strengthened" feed was stored at room temperature. The vitamin C content in the stored feed remaining during the course of storage was observed at intervals. The results are given in Table 5.

COMPARISON EXAMPLE 7

Calcium L-ascorbate was admixed at an addition rate of 0.1%, calculated as pure L-ascorbic acid, to the same feed employed in Example 5 and preservation of L-ascorbate was observed in the same manner as in Example 5. The results are given in Table 5.

COMPARISON EXAMPLE 8

The coated vitamin C preparation obtained in Comparison Example 2 was admixed at an addition rate of 0.1%, calculated as pure L-ascorbic acid, to the same feed employed in Example 5 and preservation of L-ascorbic acid was observed in the same manner as in Example 5. The results are given in Table 5.

TABLE 5

| Storage Period (hr) | Vitamin C Preservation Effect (% of Remaining Vitamin C) | | |
|---|---|---|---|
| | Example 5 | Comp. Example 7 | Comp. Example 8 |
| 1 | 100.0 | 47.4 | 78.4 |
| 3 | 99.0 | 24.5 | 64.1 |
| 5 | 95.4 | 15.1 | 49.7 |
| 12 | 91.7 | 0 | 35.7 |
| 24 | 87.8 | 0 | 0 |

From the results of Tables 4 and 5, it is seen that the coated vitamin C preparation according to the present invention exhibits an increased stability of vitamin C than the stabilized derivative of L-ascorbic acid (Ca L-ascorbate) compared to the preparation obtained by a conventional method.

We claim:

1. A coated vitamin C preparation for animal feed comprising (a) a particulate core made up of a plurality of particles containing vitamin C in an amount of at least 50% by weight, and having a particle size from 0.1 to 1,000 microns, and (b) a coating containing at least one fine powdery lipid having a melting point of at least 40° C. and vitamin E in an amount of from 0.5-6% by weight and having a particle size from 0.1 to 100 microns, said coating being formed as a layer of agglomerated particles covering each of said particles making up said particulate core, the weight ratio of the particulate core to the coating being in the range of from 1:1 to 5:1.

2. The coated vitamin C preparation of claim 1, wherein the particles making up the particulate core have a particle size in the range of from 10 to 700 microns.

3. The coated vitamin C preparation of claim 1, wherein the particle size of said particles making up the coating is from 0.5 to 50 microns.

4. A process for producing a coated vitamin C preparation for animal feed comprising the steps of colliding particles of a particulate core containing vitamin C in an amount of at least 50% by weight and having a particle size in the range of from 0.1 to 1,000 microns with particles of a coating made up of at least one fine powdery lipid having a melting point of at least 40° C., a particle size in the range of from 0.1 to 100 microns and containing vitamin E in an amount of 0.5 to 6% by weight and forming a layer of agglomerated particles of the coating particles that cover each of said particles that make up the particulate core.

5. Feed for animal culturing, said feed comprising (A) feed components and (B) a coated vitamin C preparation comprising (a) a particulate core made up of a plurality of particles containing vitamin C in an amount of at least 50% by weight, and having a particle size from 0.1 to 1,000 microns, and (b) a coating containing at least one fine powdery lipid having a melting point of at least 40° C. and vitamin E in an amount of from 0.5-6% by weight and having a particle size from 0.1 to 100 microns, and said coating being formed as a layer of agglomerated particles covering each of said particles making up said particulate core, the weight ratio of the particulate core to the coating being in the range of from 1:1 to 5:1.

6. A method of cultivating one or more animals selected from the group consisting of livestock, poultry and marine animals, said method comprising the step of feeding the animals a feed containing a pharmaceutically effective amount of a coated vitamin C preparation comprising (a) a particulate core made up of a plurality of particles containing vitamin C in an amount of at least 50% by weight, and having a particle size from 0.1 to 1,000 microns, and (b) a coating containing at least one fine powdery lipid having a melting point of at least 40° C. and vitamin E in an amount of from 0.5-6% by weight and having a particle size from 0.1 to 100 microns, said coating being formed as a layer of agglomerated particles covering each of said particles making up said particulate core, the weight ratio of the particulate core to the coating being in the range of from 1:1 to 5:1.

* * * * *